United States Patent [19]

Licciardello et al.

[11] 4,404,307
[45] Sep. 13, 1983

[54] OXOALKYL ESTERS, ORGANOLEPTIC USES THEREOF AND PROCESS FOR PREPARING SAME

[75] Inventors: Michael Licciardello, Farmingdale; Richard M. Boden, Monmouth Beach; Hugh Watkins, Lincroft; Marie R. Hanna, Hazlet, all of N.J.

[73] Assignee: International Flavors & Fragrances Inc., New York, N.Y.

[21] Appl. No.: 396,257

[22] Filed: Jul. 8, 1982

Related U.S. Application Data

[62] Division of Ser. No. 307,366, Oct. 1, 1981, Pat. No. 4,368,145.

[51] Int. Cl.³ ............................ C08K 5/09; C08K 5/10; C08K 5/12; C08K 5/13
[52] U.S. Cl. ..................................... 524/290; 524/291
[58] Field of Search .......................... 524/291, 290

[56] References Cited

U.S. PATENT DOCUMENTS 3,943,102  3/1976  Spivack et al. ............. 524/291

Primary Examiner—Joseph L. Schofer
Assistant Examiner—N. Sarofim
Attorney, Agent, or Firm—Arthur L. Liberman

[57] ABSTRACT

Described is a genus of compounds defined according to the structure:

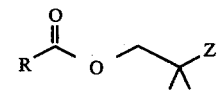

wherein Z represents carbinol having the structure:

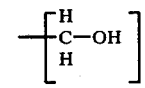

or carboxaldehyde having the structure:

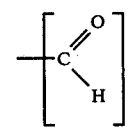

and wherein R represents 3-heptanyl or phenyl produced by (i) reacting a carboxylic acid with 2,2-dimethyl-1,3-propanediol to form the compound wherein Z represents carbinol; (ii) and then, if, desired, subsequently reacting the resulting alcohol to form an aldehyde; and organoleptic uses of such compounds in the field of perfumery, colognes and perfumed articles (e.g. perfumed polymers, or solid or liquid anionic, cationic, nonionic or zwitterionic detergents, fabric softener compositions, drier-added fabric softener articles, hair preparations, hair sprays, bath preparations and the like).

10 Claims, 17 Drawing Figures

FIG.3
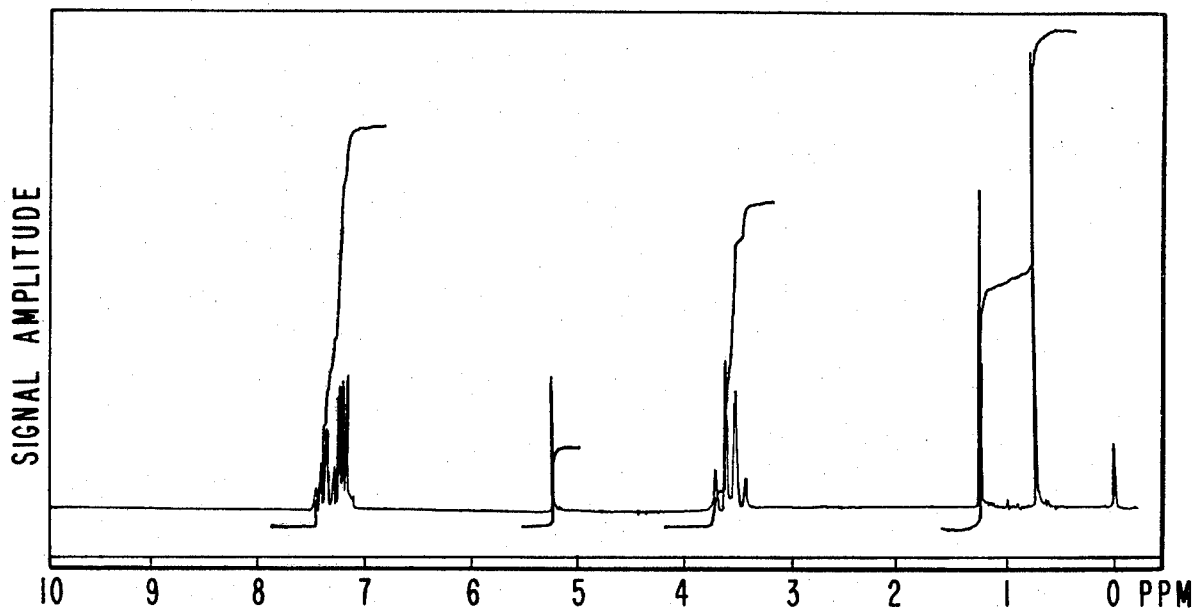
NMR SPECTRUM FOR EXAMPLE I.
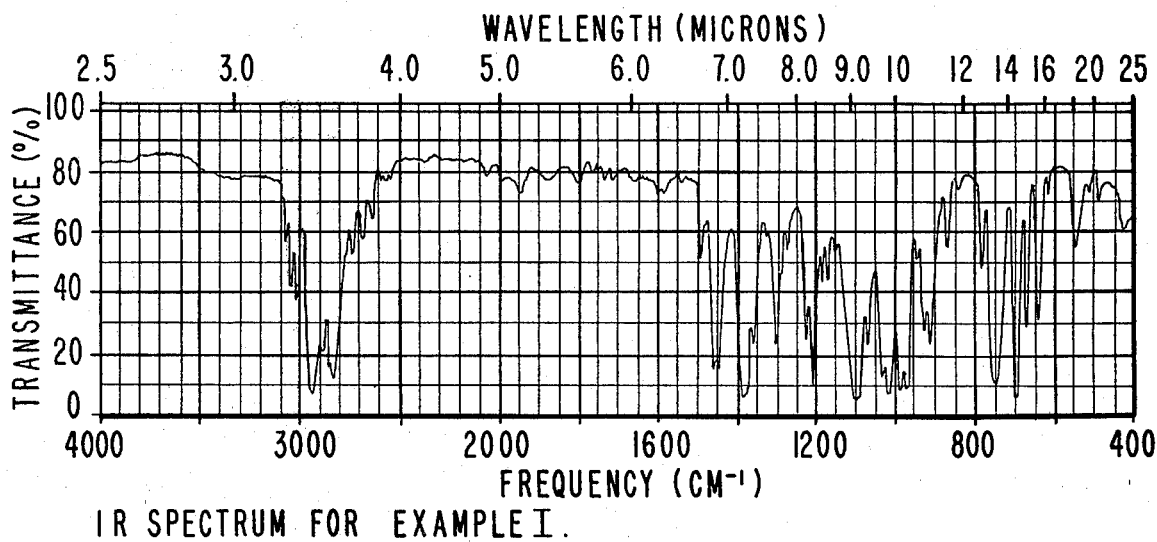
IR SPECTRUM FOR EXAMPLE I.
FIG.4

NMR SPECTRUM FOR EXAMPLE II.

IR SPECTRUM FOR EXAMPLE II.

FIG. 8
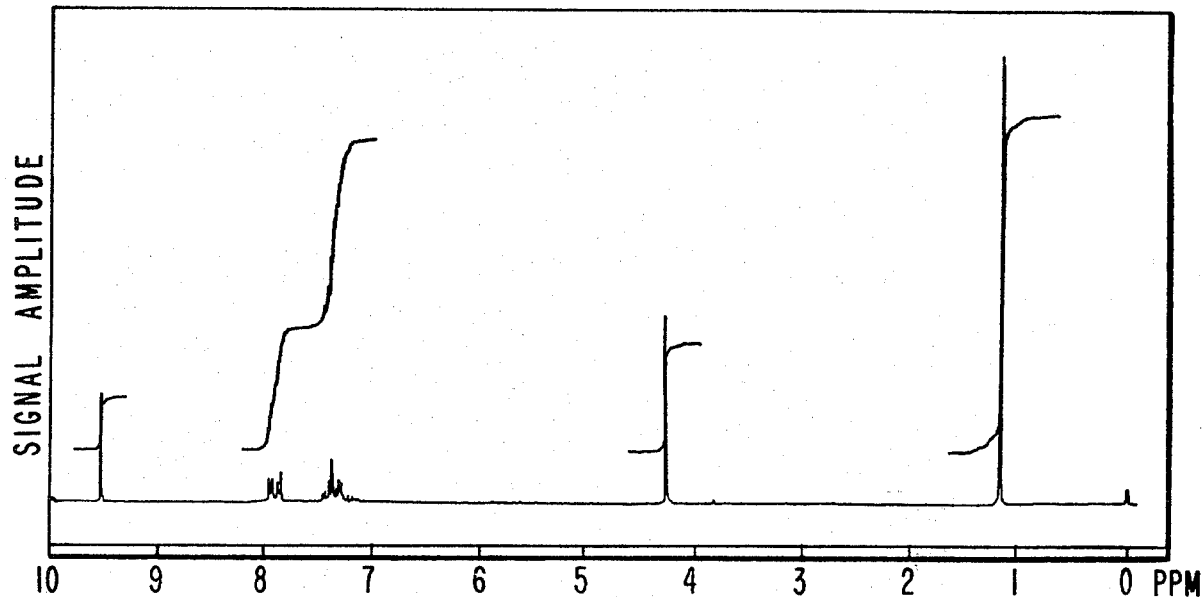
NMR SPECTRUM FOR EXAMPLE III.
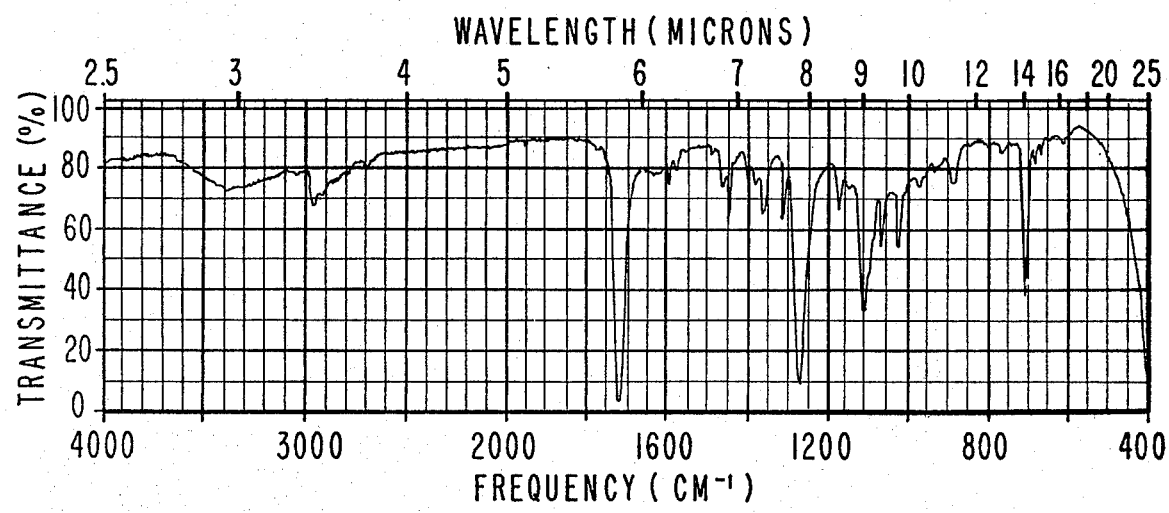
IR SPECTRUM FOR EXAMPLE III.
FIG. 9

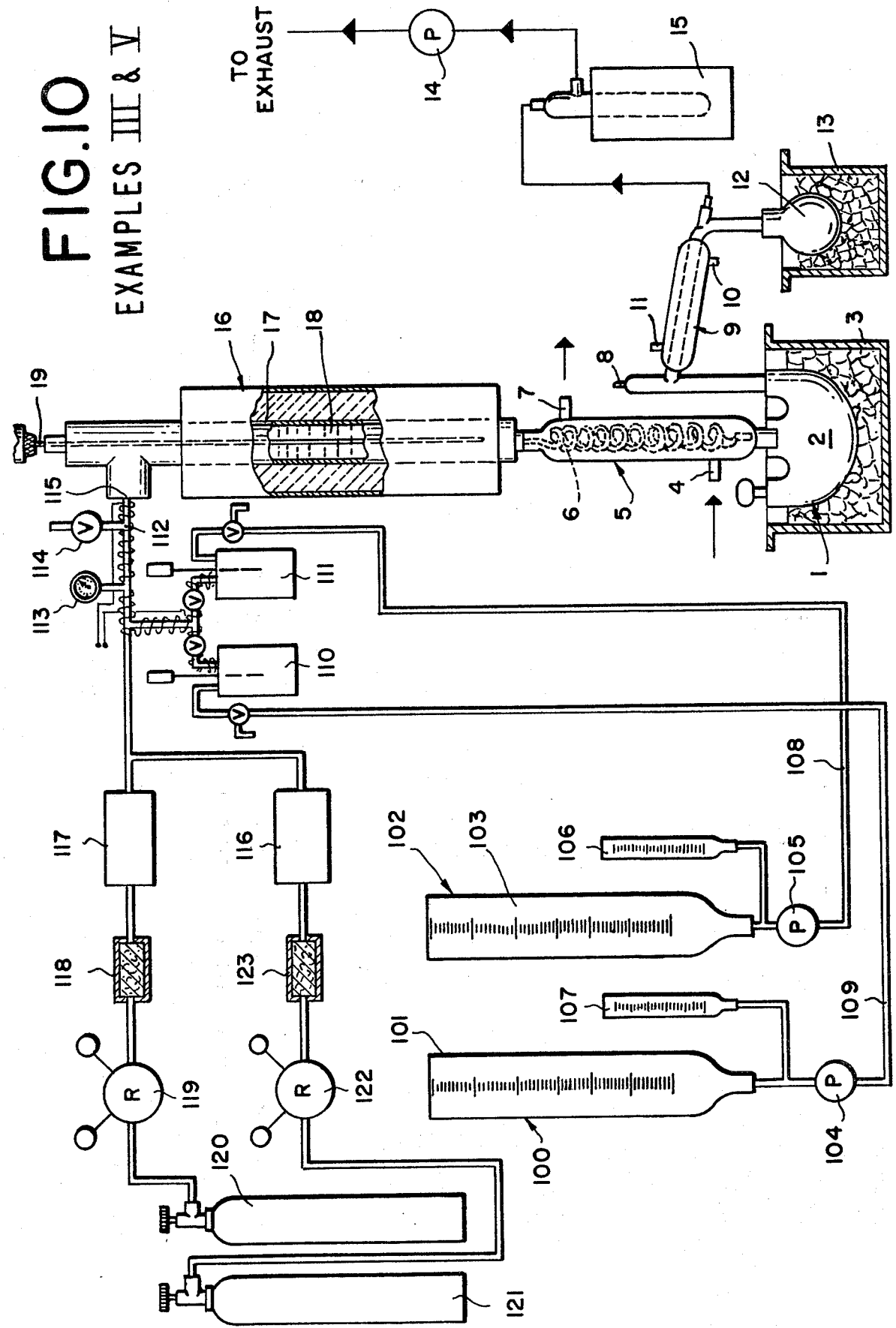

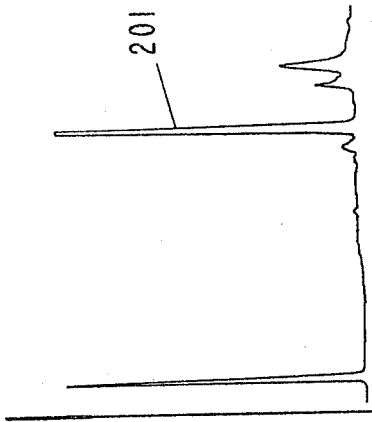
FIG.15 GLC PROFILE FOR EXAMPLE V.
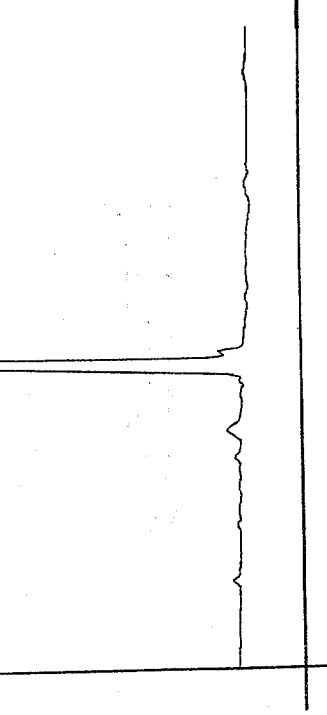
FIG.16 GLC PROFILE FOR FRACTION 1 OF EXAMPLE V.
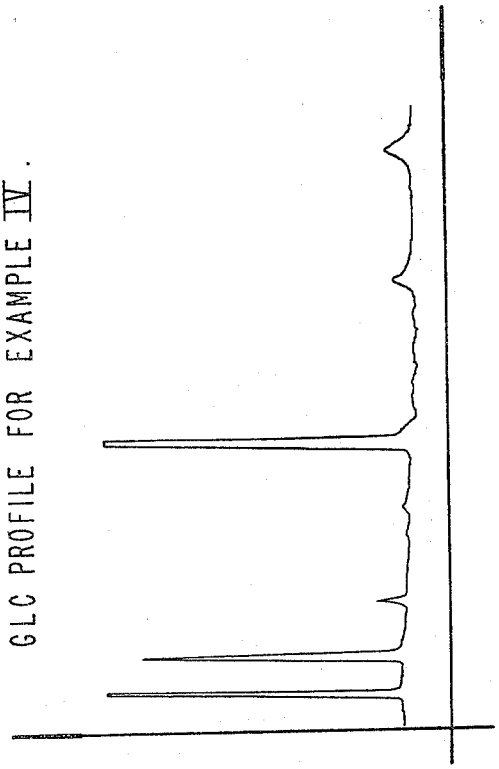
FIG.11 GLC PROFILE FOR EXAMPLE IV.
FIG.12 GLC PROFILE FOR FRACTION 3 OF EXAMPLE IV.

FIG.13
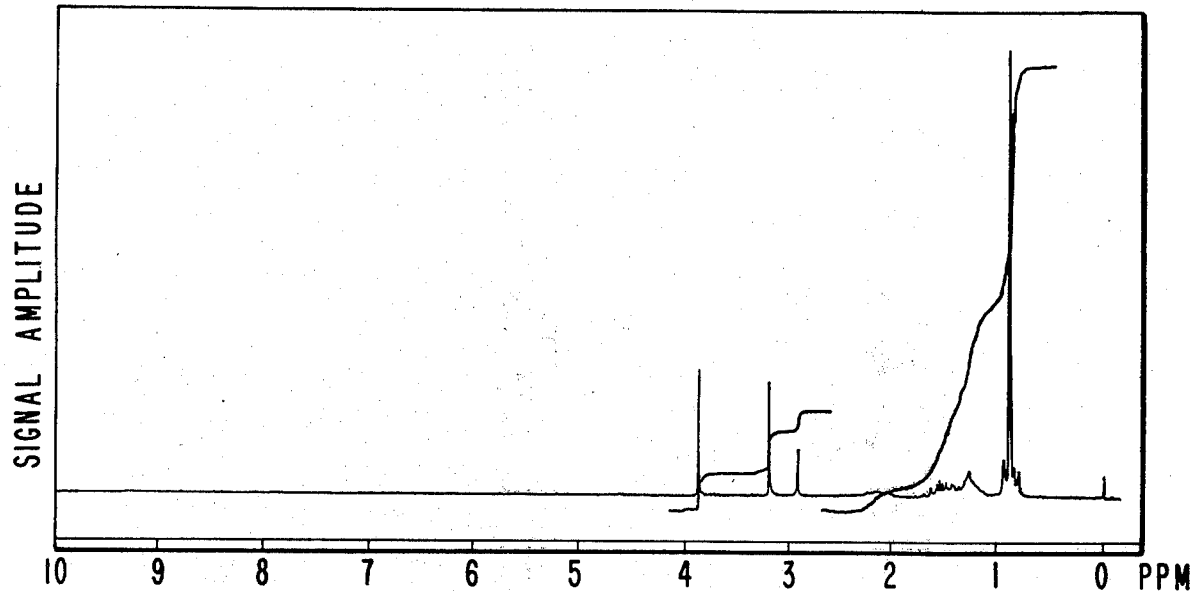
NMR SPECTRUM FOR EXAMPLE IV.
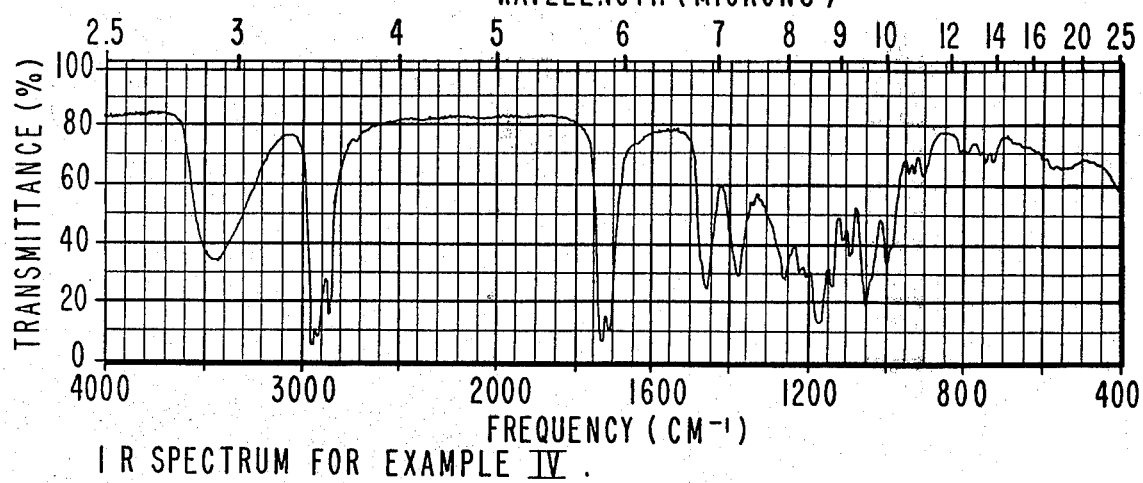
IR SPECTRUM FOR EXAMPLE IV.
FIG.14

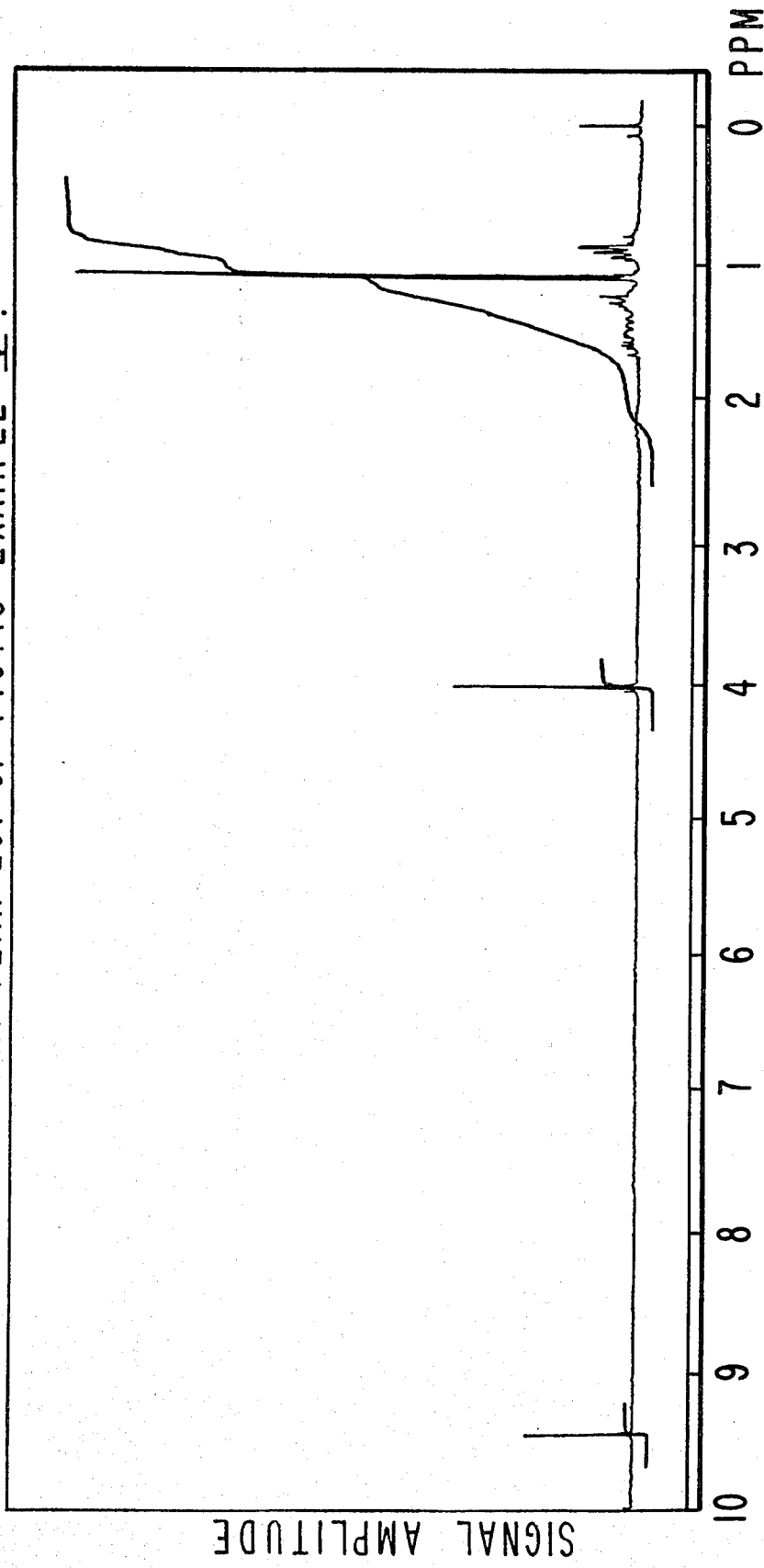
FIG.17 NMR SPECTRUM FOR TRAP PEAK 201 OF FIG.15 EXAMPLE V.

OXOALKYL ESTERS, ORGANOLEPTIC USES THEREOF AND PROCESS FOR PREPARING SAME

This is a divisional of application Ser. No. 307,366, filed Oct. 1, 1981, now U.S. Pat. No. 4,368,145.

BACKGROUND OF THE INVENTION

The instant invention relates to the compounds defined according to the generic structure:

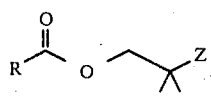

wherein Z represents carbinol having the structure:

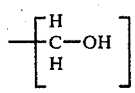

or carboxaldehyde having the structure:

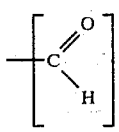

and wherein R represents 3-heptanyl or phenyl and the use of these compounds in augmenting or enhancing the aroma of perfumes, colognes and perfumed articles.

Inexpensive chemical compounds which can provide intense and long-lasting ozoney, aldehydic, floral, green, spicy (coriander-like, cardamom-like, ginger-like), fruity, honey, tobacco, coumarin-like, cumene-like and woody aromas are high desirable in the art of perfumery. Many of the natural materials which provide such fragrances and contribute such desired nuances to perfumery compositions are high in cost, unobtainable at times, vary in quality from one batch to another, have toxic properties and/or are generally subject to the usual variations of natural products.

There is, accordingly, a continuing effort to find synthetic materials which will replace, enhance or augment the fragrance notes provided by natural essential oils or compositions thereof. Unfortunately, many of the synthetic materials either have the desired nuances only to a relatively small degree or they contribute undesirable or unwanted odor to the compositions.

Oxyalkanals are known in the art of perfumery, e.g. geranoxy acetaldehyde, is a well known perfume ingredient.

Indeed, U.S. Pat. No. 3,992,457 issued on Nov. 16, 1976 discloses the use of certain oxyalkanals as intermediates in the production of compounds useful in perfumery. These oxyalkanals are prepared according to the reaction:

The compounds of the prior art, however, do not have the advantageous and unobvious properties in the perfume industry that the compounds of the instant application having the above defined generic structure have.

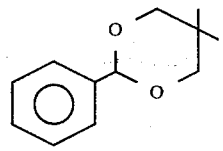

Figure 2:
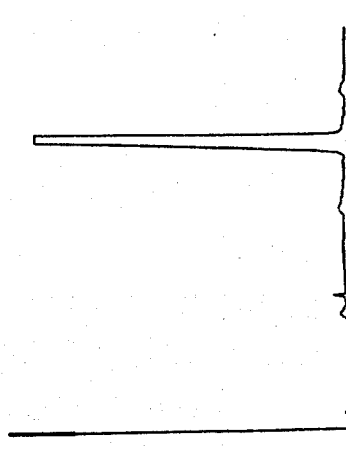

FIG. 2 is the GLC profile for fraction 3 of the distillation product of the reaction product of Example I containing the compound having the structure:

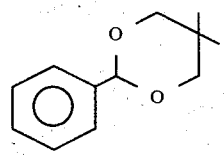

FIG. 3 is the NMR spectrum for the distillation product of the reaction product of Example I which consists of the compound having the structure:

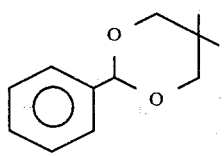

FIG. 4 is the infra-red spectrum for the distillation product of the reaction product of Example I consisting of the compound having the structure:

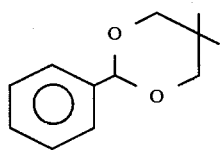

Figure 5:
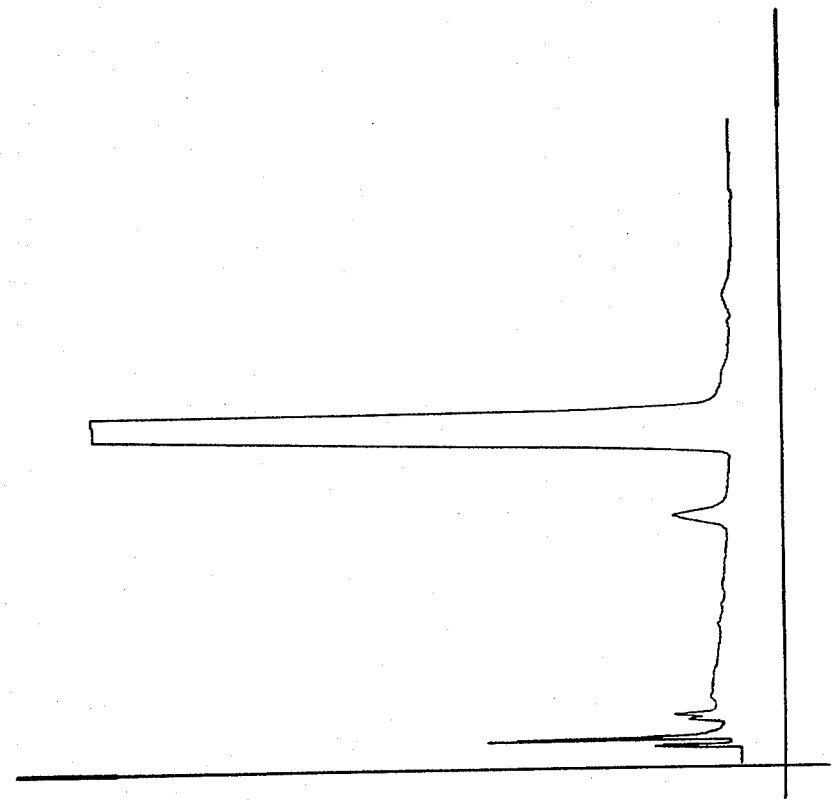

FIG. 5 is the GLC profile for the reaction product of Example II consisting of the compound having the structure:

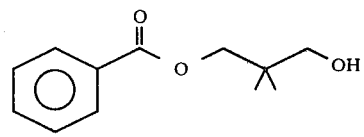

Figure 6:
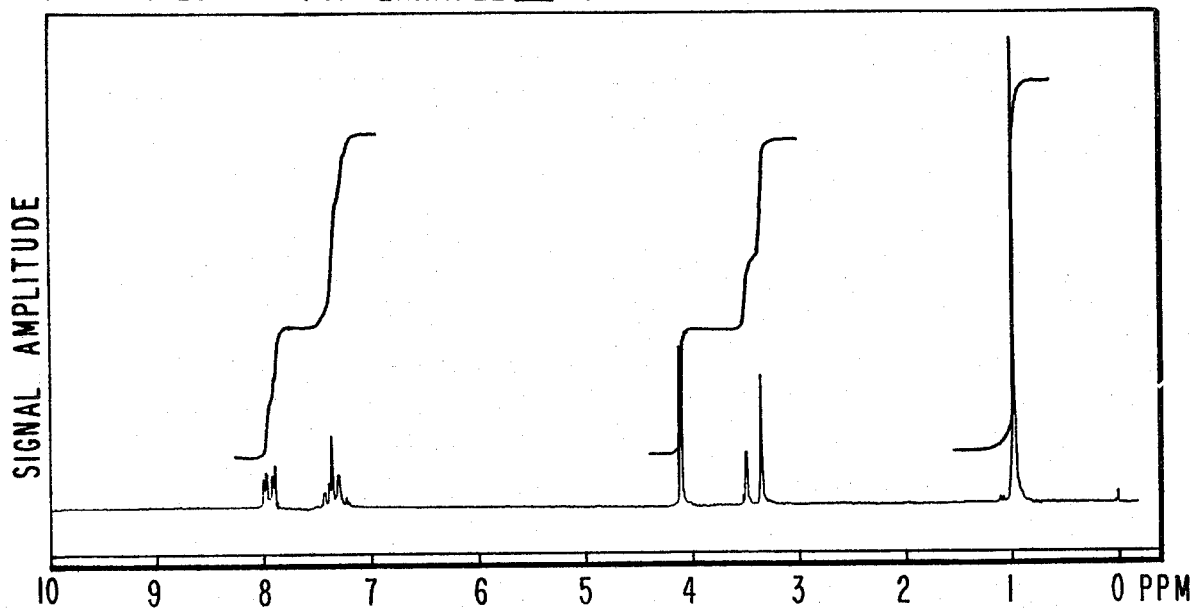

FIG. 6 is the NMR spectrum for the distillation product of the reaction product of Example II consisting of the compound having the structure:

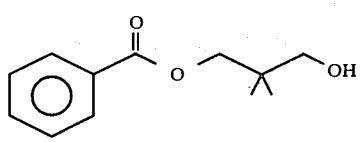

Figure 7:
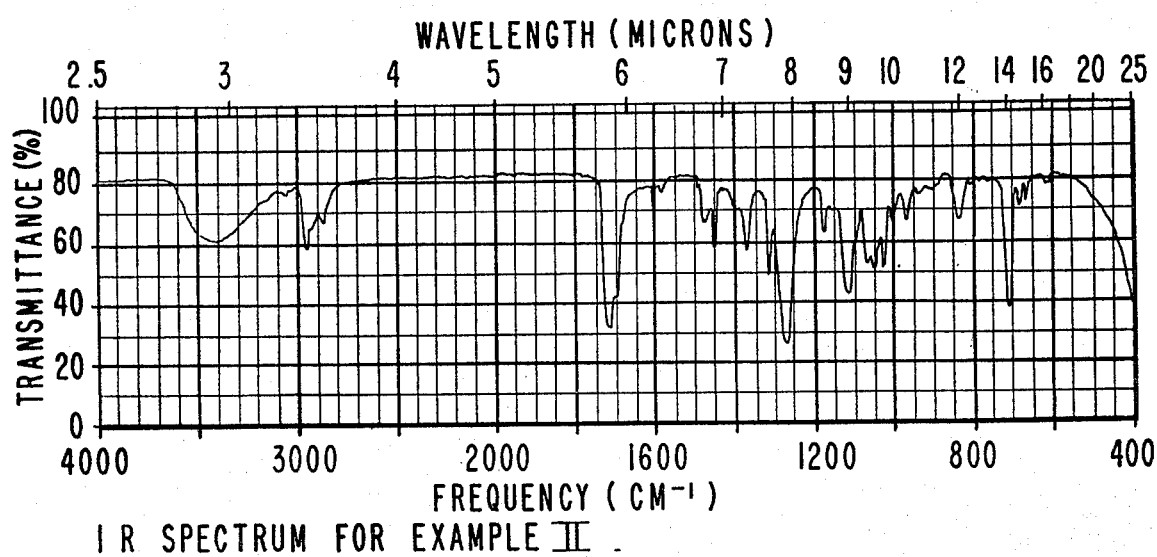

FIG. 7 is the infra-red spectrum for the distillation product of the reaction product of Example II consisting of the compound having the structure:

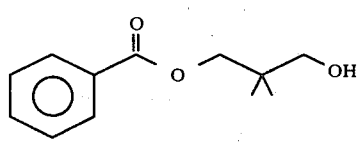

FIG. 8 is the NMR spectrum for the distillation product of the reaction product of Example III consisting of the compound having the structure:

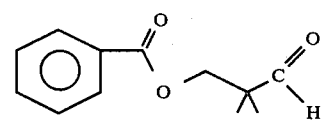

FIG. 9 is the infra-red spectrum for the distillation product of the reaction product of Example III consisting of the compound having the structure:

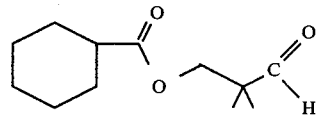

FIG. 10 is a schematic diagram of the apparatus used in order to carry out the oxidation reactions of Examples III and V in order to effect the chemical reactions:

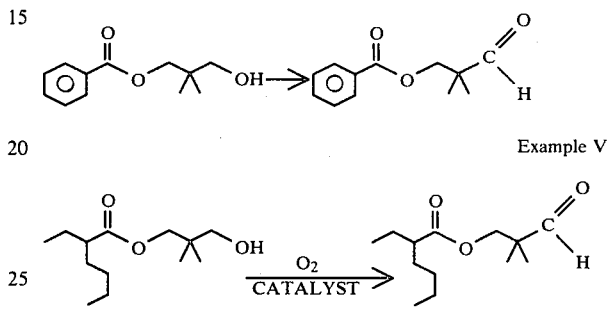

showing the production of aldehydes by oxidizing alcohols.

FIG. 11 is the GLC profile of the reaction product of Example IV containing the compound having the structure:

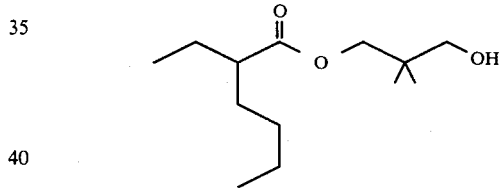

FIG. 12 is the GLC profile for fraction 3 of the distillation product of the reaction product of Example IV consisting of the compound having the structure:

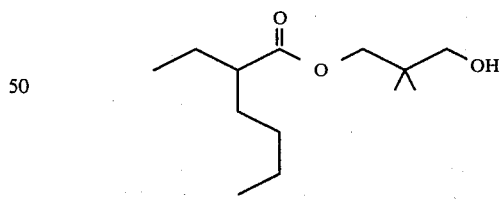

FIG. 13 is the NMR spectrum for fraction 3 of the distillation product of the reaction product of Example IV containing the compound having the structure:

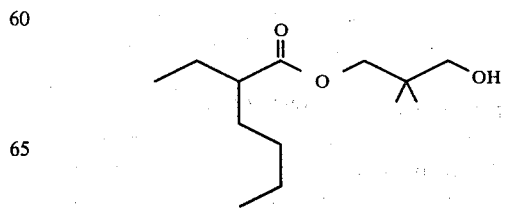

FIG. 14 is the infra-red spectrum for the distillation product of the reaction product of Example IV containing the compound having the structure:

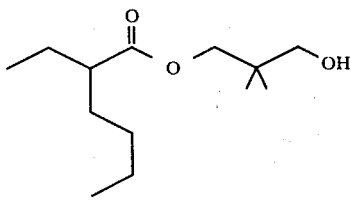

FIG. 15 is the GLC profile for the reaction product of Example V containing the compounds having the structure:

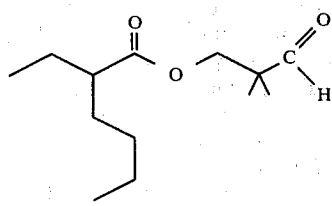

FIG. 16 is the GLC profile for the distillation product (fraction 1) of the reaction product of Example V consisting of the compound having the structure:

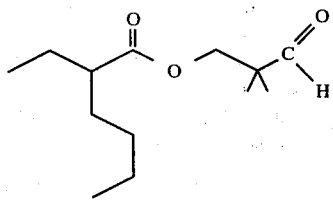

(conditions: SE-30 column programmed at 100°-220° C.).

FIG. 17 is the NMR spectrum for the trap of peak 101 of the GLC profile of FIG. 14 which is the compound having the structure:

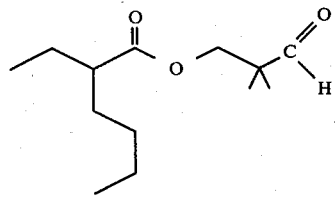

DETAILED DESCRIPTION OF THE DRAWINGS

FIG. 10 represents a schematic diagram of the process equipment for carrying out the processes of Example III for effecting the reaction:

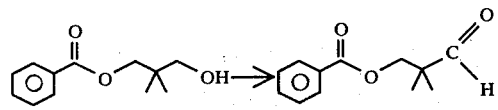

and for Example V effecting the reaction:

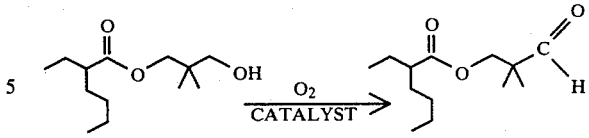

wherein specific alcohols are oxidized over a silver catalyst to form specific aldehydes.

In each case, organic reactant feed 100 which is the alcohol reactant defined according to one of the structures:

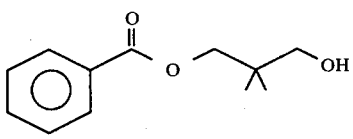
Example III

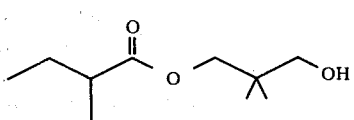
Example V held in holding tank 101 calibrated according to calibration apparatus 107 using pump 104 is fed through tube 109 simultaneously with water feed 103 held in holding tank 102 calibrated by calibration apparatus 106 (using pump 105 for the water feed and tube 108 for the water feed) through vaporizers 110 (for the alcohol feed) and 111 (for the water feed) (wherein the mixture is heated) and then through heated tube 112 equipped with pressure gauge 113 and relief valve 114 into reaction tube 17 containing catalyst 18 (the reaction tube being heating using a cylindrical furnace 16 at 115). The catalyst bed 18 is rotated as a result of rotation of the rotatable rod 19. Simultaneously, air held in pressurized cylinder 120 under pressure and nitrogen held in pressurized cylinder 121 are pumped through regulator 119 (for the air) and regulator 122 (for the nitrogen) and filter 118 (for the air) and filter 123 (for the nitrogen) using mass flow controller 117 (for the air) and mass flow controller 116 (for the nitrogen) into heated tube 112 thereby creating a mixture at 112 of air, nitrogen, one of the compounds defined according to one of the structures:

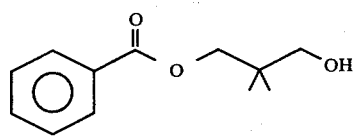
Example III

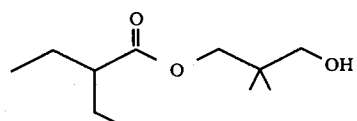
Example V and water vapor. The reaction mixture passes through catalyst bed 18 through condensation coil 6 which is cooled using cooling water entering the heat exchanger 5 at location 4 and exiting at location 7. The condensed reaction product which is one of the aldehydes:

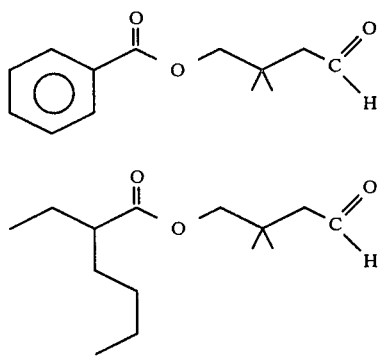

Example III

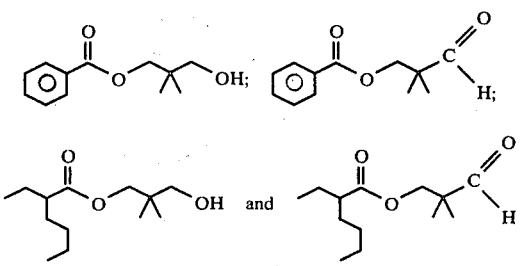

Example V is retained in flask 2 in location 1, flask 2 being cooled using ice bath 3. Vacuum source 14 is used to assist the flow of the organic feed, the water feed, the nitrogen and the air or oxygen through reactor 17 into flask 2. Volatiles are condensed in flask 12, cooled by dry ice bath 13, and in the Dewar dry ice bath 15. Assisting in the cooling of the volatiles not retained in flask 2 is heat exchanger 9 wherein water is used as a coolant entering the heat exchanger at location 10 and exiting from the heat exchanger at location 11.

THE INVENTION

The present invention provides the oxoalkyl esters defined according to the structure:

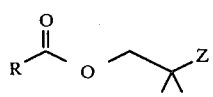

wherein A represents 3-heptanyl having the structure:

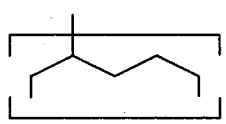

or phenyl and Z represents carbinol having the structure:

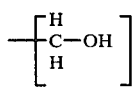

or carboxaldehyde having the structure:

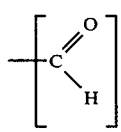

specifically defining the four compounds having the structures:

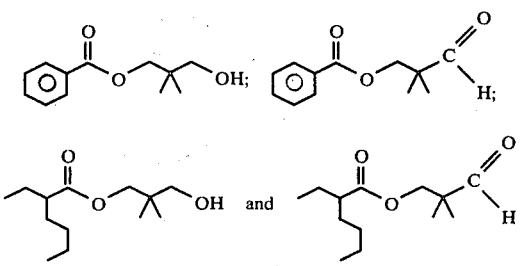

The composititons of matter of our invention produced according to the process of our invention are capable of augmenting, enhancing or providing ozoney, aldehydic, floral, green, spicy (coriander-like, cardamom-like, ginger-like), fruity, honey-like, tobacco, coumarin-like, cumene-like and woody aroma profiles in perfume compositions, colognes and perfumed articles (e.g. perfume polymers E P or G, acrylic polymers, solid or liquid anionic, cationic, nonionic or zwitterionic detergents, fabric softener articles, fabric softener compositions, drier-added fabric softener articles, cosmetic powders, hair preparations, bath preparations, e.g. bath oils and shampoos and the like).

The substances of our invention are produced by first reacting an appropriate aldehyde with 2,2-dimethyl-1,3-propanediol to form either a hydroxalkyl ester or a cyclic acetal depending on whether benzaldehyde is used as a reactant or whether the initial reactant is a carboxylic acid derivative such as 2-ethyl-hexanoic acid.

Thus, in carrying out the reaction between an aldehyde such as benzaldehyde and 2,2-dimethyl-1,3-propanediol, the first substance which is produced is the cyclic acetal according to the reaction:

In order to produce the hydroxyalkyl ester having the structure:

it is then necessary to oxidize this cyclic acetal using an oxidizing agent. Such an oxidizing agent is an alkali metal hypochlorite, for example, sodium hypochlorite. Thus, when using such an oxidizing agent, the reaction from the cyclic acetal to the hydroxalkyl ester is thus:

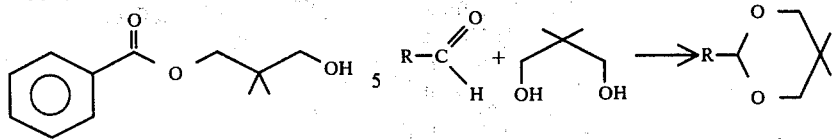

The resulting alcohol can be used "as is" for its organoleptic properties or it can be further oxidized to form the aldehydes of our invention according to, for example, the reaction:

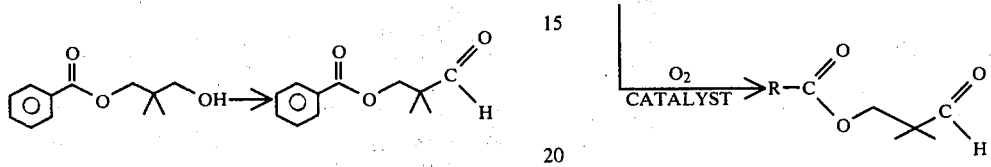

On the other hand, instead of using as a starting material an aldehyde, an alkanoic acid can be used, and in this case, the hydroxyalkyl ester is formed directly by reacting 2,2-dimethyl-1,3-propanediol with, for example, 2-ethylhexanoic acid in the presence of an acid catalyst or an esterification catalyst, thusly:

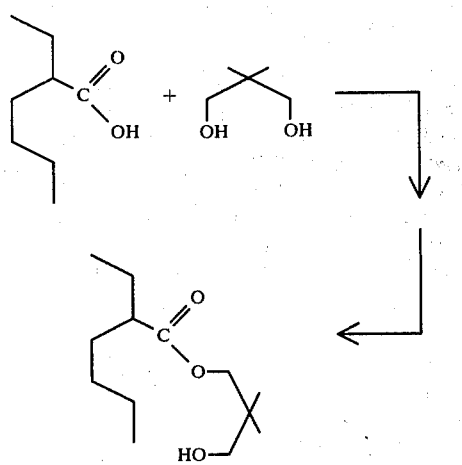

The resulting hydroxyalkyl ester can be used "as is" or it, too, can be further oxidized using oxygen or air to the aldehyde of our invention having the structure:

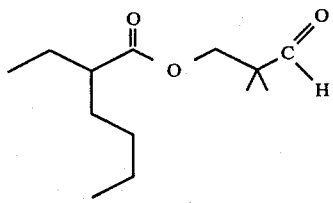

In general, when an aldehyde is used as a starting material, the reaction must go through the cyclic acetal prior to oxidation thereof to form the hydroxyalkyl ester which is then oxidized, if preferred, to the aldehyde according to the general reaction:

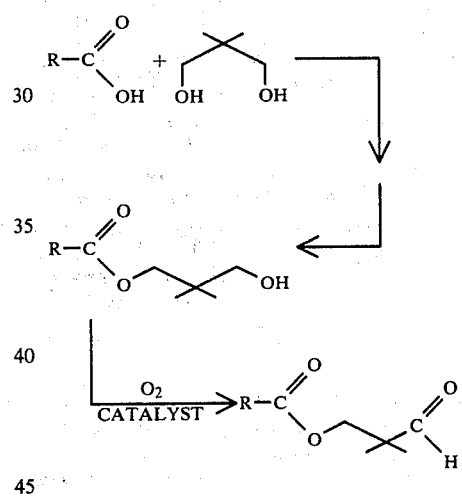

When an alkanoic acid or benzoic acid is used as a starting material, in reacting with the 2,2-dimethyl-1,3-propanediol, the hydroxyalkyl ester is formed directly according to the following reaction:

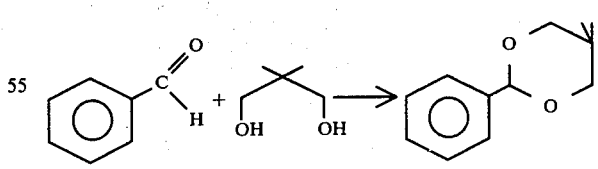

wherein R represents 3-heptyl or phenyl.

The process of our invention using the aldehyde as a starting material

The initial reaction to form the cyclic acetal thusly:

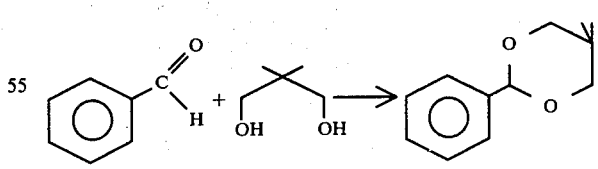

(for example) preferably takes place at reflux conditions and most economically at atmospheric pressure. It is preferred that the mole ratio of aldehyde:2,2-dimethyl-1,3-propanediol be between 1.5 moles diol:0.5 moles aldehyde up to 0.5 moles diol:1.5 moles aldehyde with a most preferred mole ratio of diol:aldehyde of about 1:1 (with, however, a slight excess of diol over aldehyde). The reaction should take place in the presence of a solvent which is inert to the reactants and such solvents are toluene and xylene. The solvent should be such that its boiling point at atmospheric pressure is sufficient to cause the reaction to proceed in a reasonable amount of time with a relatively high (greater than 50%) yield of product. Thus, when using toluene as a solvent, the reaction proceeds at a temperature of between 100° and 140° C. depending upon the pressure over the reaction mass during the reaction procedure.

The oxidation of the cyclic acetal to form the hydroxyalkyl ester according to, for example, the reaction:

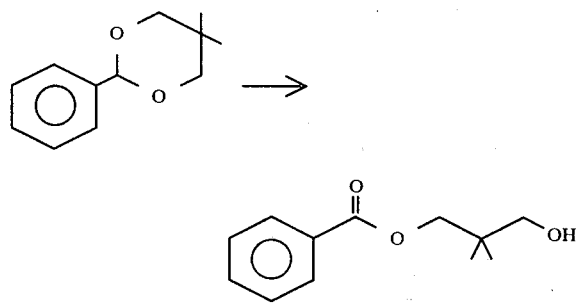

preferably takes place at a temperature of between 10° C. and 40° C.; most preferably at room temperature, e.g. 22°–30° C. at atmospheric pressure. The mole ratio of oxidizing agent:cyclic acetal is preferably 1:1 with a slight excess of cyclic acetal over the oxidizing agent to ensure that no residual oxidizing agent remains in the reaction product. Thus, for example, when reacting the benzaldehyde neopentyl acetal with hypochlorite solution, it is most preferred to use a 10% sodium hypochlorite solution to react with the benzaldehyde neopentyl acetal and it is also preferred to use a weak acid medium (e.g. a pH of between about 2 and 5). In order to effect such a pH range in the reaction mass, it is preferred to use acetic acid although propionic acid or butyric acid or dilute chloroacetic acid may also be used in order to adjust the pH. In addition, one molar ammonium chloride may be used in place of the acetic acid in order to effect this pH range of the reaction mass.

No matter which way the hydroxyalkyl ester is produced, the conversion of the hydroxyalkyl ester to the desired ester-aldehyde derivative is carried out in the same way; using oxygen or air and a silver catalyst or a copper chromite catalyst at a temperature in the range of from 200°–500° C. (atmospheric pressure).

Thus, the oxidation reaction to form the aldehyde:

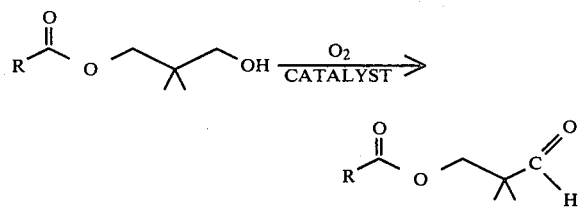

wherein R represents 3-heptyl or phenyl is preferably carried out in apparatus described in the "Detailed Description of the Drawings" section of the instant specification, supra, and schematically shown in FIG. 5. The oxidation may use either air or oxygen. The oxidation catalyst may either be silver or copper chromite (CU-CRO₃).

The reaction temperature may vary from 200° C. up to 500° C. but the temperature is dependent upon the desired yield and required residence time of the mixture of compounds defined according to the structure:

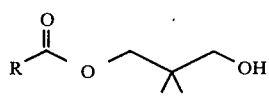

in contact with the solid catalyst. Necessarily, the reaction is vapor phase and the surface area of catalyst and flow rate of reactants as well as residence time and reaction temperature and pressure are all important variables which must be optimized in relation to one another if yield and conversion of product are to be optimized. It is preferred that the reaction be carried out in the presence of water vapor and it is also preferred that the water flow rate and flow rate of alcohol reactant be approximately equal. The gas flow rates may vary between 50 and 400 ml per minute with a preferred oxygen flow rate of 210–300 ml per minute at a temperature of reaction of 450° C.; a liquid alcohol flow rate of about 2 ml per minute and a water flow rate of about 2 ml per minute. The yield using the foregoing conditions of product defined according to the generic structure:

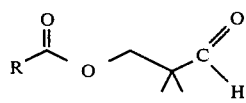

wherein R is 3-heptyl or phenyl is approximately 50%. Separation of the aldehyde product from the alcohol reactant and recycling of the alcohol reactant will, of course, raise the yield. A higher temperature of reaction e.g. 500° C. and longer residence time (e.g. greater distance of travel of reactant through catalyst and/or area of contact with catalyst) will raise the yield to approximately 80%, the higher residence time being approximately 20% greater than what is used in either of Examples III or V.

REACTION SEQUENCE COMMENCING WITH THE USE OF A CARBOXYLIC ACID AS A STARTING MATERIAL

When commencing with the use of a carboxylic acid as a reactant, for example in the reaction:

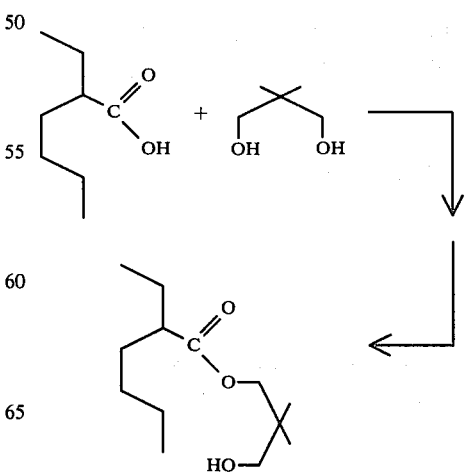

whereat the hydroxyl ester is made directly rather than going through a cyclic acetal followed by an oxidation reaction, although the reaction is more simplified, the yields will be necessarily lesser in view of the reaction equilibrium constant being lesser.

This reaction is also to take place in the presence of an inert solvent such as toluene at reflux conditions. Although the nature of the particular solvent is not critical, too low a boiling point will yield an unnecessary lengthy period of time of reaction. Accordingly, toluene is the ideal solvent to use in this reaction in view of its boiling point at atmospheric pressure and in view of the fact that it is preferred to carry out the reaction at temperatures of between 80° and 150° C. at atmospheric pressure.

The mole ratio of carboxylic acid:2,2-dimethyl-1,3-propanediol may vary from 1:2 up to 2:1 with a preferred mole ratio of carboxylic acid:2,2-dimethyl-1,3-propanediol of 1:2. The esterification reaction is to be carried out in the presence of an esterification catalyst such as sulfuric acid or paratoluene sulfonic acid. The concentration of sulfuric acid catalyst or paratoluene sulfonic acid catalyst in this esterification reaction may vary from 0.001 molar up to 0.1 molar.

The resulting hydroxyalkyl ester is distilled from the reaction mass in which it is formed and either used as is for its organoleptic properties or further reacted via an oxidation reaction using air or oxygen in the presence of a silver or copper chromite catalyst in the apparatus as set forth in FIG. 10 and as described in the Detailed Description of the Drawings, supra. The details of this oxidation reaction are set forth supra.

Examples of the oxoalkyl esters of our invention and their organoleptic properties are set forth in the following Table I.

TABLE 1

| Structure of Oxoalkyl Ester | Organoleptic Properties |
| --- | --- |
| [structure] | Ozoney, aldehydic, floral, green, spicy (coriander-like, cardamom-like, giner-like). |
| [structure] | A fruity aroma. |
| [structure] | A honey, tobacco aroma with coumarin-like, and cumene-like notes. |
| [structure] | A fruity, woody aroma. |

One or more oxoalkyl esters prepared in accordance with the process of our invention and one or more auxiliary perfume ingredients including, for example, alcohols other than the oxoalkyl esters of our invention, aldehydes other than the oxoalkyl esters of our invention, ketones, terpenic hydrocarbons, nitriles, esters other than the oxoalkyl esters of our invention, lactones, natural essential oils and synthetic essential oils may be admixed so that the combined odors of the individual components produce a pleasant and desired fragrance particularly and preferably in the spice-type fragrances. Such perfume compositions usually contain (a) the main note or "bouquet" or foundation stone of the composition; (b) modifiers which round off and accompany the main notes; (c) fixatives which include odorous substances which lend a particular note to the perfume throughout all states of evaporation and substances which retard evaporation; and (d) topnotes which are usually low-boiling, fresh-smelling materials.

In perfume compositions, it is the individual components which contribute their particular olfactory characteristics, however, the overall sensory effect of the perfume composition will be at least the sum total of the effects of each of the ingredients. Thus, the oxoalkyl ester compositions prepared in accordance with the process of our invention can be used to alter, modify or enhance the aroma characteristics of a perfume composition, for example, by utilizing or moderating the olfactory reaction contributed by another ingredient in the composition.

The amount of the oxoalkyl ester compositions prepared in accordance with the process of our invention which will be effective in perfume compositions as well as in perfumed articles (e.g. perfumed polymers, anionic, cationic, nonionic or zwitterionic detergents, soaps, fabric softener compositions, fabric softener articles, bath preparations and hair preparations and the like) and colognes depends upon many factors including the other ingredients, their amounts and the effects which are desired. It has been found that perfume compositions containing as little as 0.01% of the oxoalkyl ester compositions prepared in accordance with the process of our invention or even less (e.g. 0.005%) can be used to impart ozoney, aldehydic, floral, green, spicy (coriander-like, cardamom-like, ginger-like) fruity, honey, tobacco-like, coumarin-like, cumene-like and woody aroma nuances to soaps, microporous polymers, cosmetics, anionic, cationic, nonionic or zwitterionic detergents, fabric softener compositions, fabric softener articles, bath preparations, hair preparations and other products. The amount employed can range up to 70% of the fragrance components and will depend on considerations of cost, nature of the end product, the effect desired in the finished product and the particular fragrance sought.

The oxoalkyl ester compositions prepared in accordance with the process of our invention are useful (taken alone or taken together with other ingredients in perfume compositions) as (an) olfactory component(s) in detergents and soaps, space odorants and deodorants, perfumed polymers, perfumes, colognes, toilet water, bath preparations such as creams, deodorants, hand lotions and sun screens, powder such as talcs, dusting powders, face powders and the like. When used as (an) olfactory component(s) as little as 0.005% of the oxoalkyl ester compositions prepared in accordance with the process of our invention will suffice to impart an ozoney, aldehydic, floral, green, spicy (coriander-like, cardamom-like, ginger-like) fruity, honey, tobacco, coumarin-like, cumene-like and woody aroma to spice formulations and spice-type aromas. Generally, no more than 6% of the oxoalkyl ester compositions of our invention based on the ultimate end product is required in the perfumed article.

In addition, the perfume composition or fragrance composition of our invention can contain a vehicle or carrier for the oxoalkyl ester compositions prepared in accordance with the process of our invention. The vehicle can be a liquid such as a non-toxic alcohol (e.g. ethyl alcohol), a non-toxic glycol (e.g. 1,2-propylene glycol) or the like. The carrier can also be an absorbent solid such as a gum (e.g. gum arabic, xanthan gum or the like) or components for encapsulating the compositions such as gelatin as by coacervation or such as other polymers such as urea formaldehyde polymers for the purpose of encapsulation by means of formation of capsules having polymeric walls.

It will thus be apparent that the oxoalkyl ester compositions prepared in accordance with the process of our invention can be utilized to alter, modify or enhance the sensory properties particularly organoleptic properties, such as as fragrances, of a wide variety of consumable materials.

The following Examples I–V set forth means for synthesizing precursors for use in synthesizing the products of our invention as well as the products of our invention themselves. The examples including VI and subsequent thereto serve to illustrate the organoleptic utilities of the oxoalkyl esters of our invention.

All parts and percentages given herein are by weight unless otherwise specified.

EXAMPLE I

Preparation of Neopentyl Acetal of Benzaldehyde

Reaction:

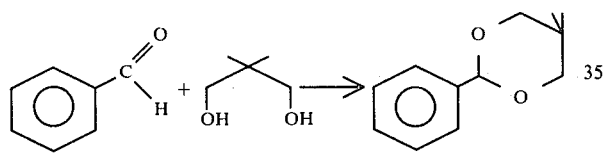

Into a 3 liter reaction flask equipped with heating mantle, thermometer, Bidwell trap, reflux condenser, and nitrogen blanket apparatus is placed 1000 grams of benzaldehyde (9.4 moles), 1,100 grams of neopentyl alcohol (2,2-dimethyl-1,3-propanediol) (10.5 moles), 250 ml toluene and 10 grams of paratoluene sulfonic acid. The reaction mass is heated to reflux and refluxed while removing water at 99°–140° C. for a period of 2.5 hours. At the end of the 2.5 hours, the reaction mass is cooled to room temperature, transferred to a separatory funnel and washed as follows:
1. two one-liter volumes of water
2. two one-liter volumes of saturated sodium chloride solution.

The organic layer is then distilled on a 6″ stone column yielding the following fractions:

| Fraction Number | Vapor Temp. (°C.) | Liquid Temp. (°C.) | Pressure mm/Hg | Reflux Ratio | Weight of Fraction (grams) |
|---|---|---|---|---|---|
| 1 | 25/72 | 10/118 | 3.0/3.0 | RO | |
| 2 | 97 | 118 | 3.0 | RO | 93 |
| 3 | 97 | 118 | 3.0 | RO | 97 |
| 4 | 97 | 118 | 3.0 | RO | 101 |
| 5 | 97 | 120 | 3.0 | RO | 219 |
| 6 | 105 | 123 | 3.7 | RO | 225 |
| 7 | 105 | 123 | 3.8 | RO | 233 |
| 8 | 97 | 125 | 3.0 | RO | 104 |
| 9 | 103 | 128 | 3.4 | RO | 114 |
| 10 | 109 | 150 | 3.0 | RO | 124 |

| Fraction Number | Vapor Temp. (°C.) | Liquid Temp. (°C.) | Pressure mm/Hg | Reflux Ratio | Weight of Fraction (grams) |
|---|---|---|---|---|---|
| 11 | 112 | 185 | 3.0 | RO | — |

Fractions 2–11 are bulked and used for the process of Example II.

Figure 1:
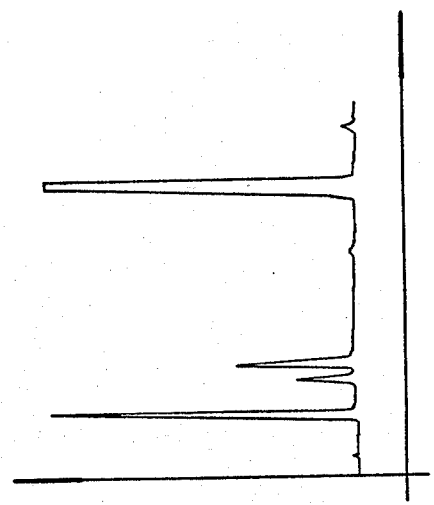
FIG. 1 is the GLC profile for the reaction product of Example I which contains the compound having the structure.

FIG. 1 is the GLC profile for the reaction product prior to distillation.

FIG. 2 is the GLC profile for fraction 3 of the foregoing distillation.

FIG. 3 is the NMR spectrum for bulked fractions 2–11 of the foregoing distillation containing the compound having the structure:

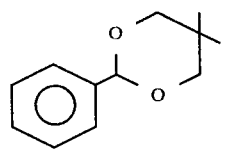

FIG. 4 is the infra-red spectrum for bulked fractions 2–11 of the foregoing distillation containing the compound having the structure:

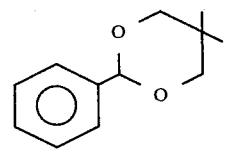

EXAMPLE II

Neopentanol Benzoate (2,2-Dimethyl-1,3-Propanediol-Monobenzoate)

Reaction:

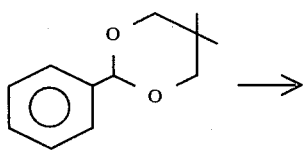

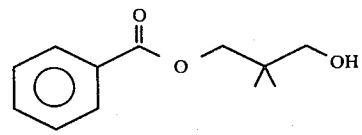

Into a 5 liter reaction flask equipped with stirrer, thermometer, reflux condenser, dropping funnel and cooling bath is placed 310 grams of acetic acid and 500 grams of benzaldehyde neopentyl acetal having the structure:

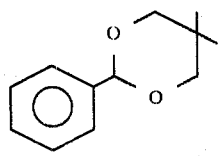

prepared in accordance with the process of Example I, supra, bulked fractions 2-11. The resulting mixture is cooled to 20°-25° C.

Into the dropping funnel is placed 2,220 grams of a 10% solution of sodium hypochlorite.

Over a period of 4 hours the sodium hypochlorite solution is added to the mixture of acetic acid and benzaldehyde neopentyl acetal while maintaining the temperature of the reaction mass at 20°-29° C., with stirring. At the end of the 4 hour period, the reaction is completed and the reaction mass is poured into 1,000 ml of a 10% aqueous salt solution admixed with 500 ml of methylene chloride. The resulting mixture now separates into two phases, an organic phase and an aqueous phase. The organic phase is separated from the aqueous phase and the organic phase is washed with one liter of 5% sodium hydroxide followed by two one-liter portions of water. The reaction mass is then distilled on a 24" Goodloe 1" diameter column yielding the following fractions:

| Fraction Number | Vapor Temp. (°C.) | Liquid Temp. (°C.) | Pressure mm/Hg | Reflux Ratio | Weight of Fraction (grams) |
|---|---|---|---|---|---|
| 1 | 109/120 | 157/160 | .9/.9 | 9:1/9:1 | 21.5 |
| 2 | 120 | 160 | .9 | 9:1 | 23.8 |
| 3 | 120 | 160 | .7 | 9:1 | 22.5 |
| 4 | 118 | 159 | .6 | 9:1 | 17.6 |
| 5 | 116 | 160 | .6 | 4:1 | 23.2 |
| 6 | 116 | 160 | .4 | 4:1 | 22.5 |
| 7 | 115 | 161 | .3 | 4:1 | 19.8 |
| 8 | 115 | 161 | .3 | 4:1 | 24.5 |
| 9 | 115 | 161 | .3 | 9:1 | 28.9 |
| 10 | 115 | 161 | .3 | 9:1 | 22.2 |
| 11 | 115 | 163 | .3 | 9:1 | 23.3 |
| 12 | 120 | 164 | .3 | 2:1 | 27.7 |
| 13 | 130 | 167 | .3 | 2:1 | 61.1 |
| 14 | 128 | 172 | .3 | 2:1 | 51.0 |
| 15 | 103 | 220 | .3 | 0 | 47.9 |

Fractions 2-12 are bulked for use in performing Example III.

FIG. 5 is the GLC profile for the reaction mass prior to distillation containing the compound having the structure:

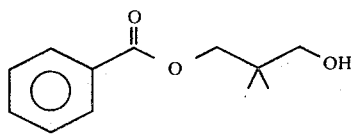

FIG. 6 is the NMR spectrum for bulked fractions 2-11 for the foregoing distillation containing the compound having the structure:

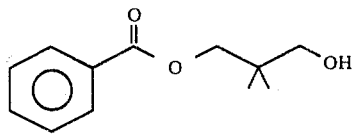

FIG. 7 is the infra-red spectrum for bulked fractions 2-11 of the foregoing distillation containing the compound having the structure:

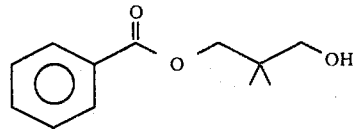

EXAMPLE III

Preparation of 3-Benzoyloxy-2,2-Dimethylpropanal

Reaction:

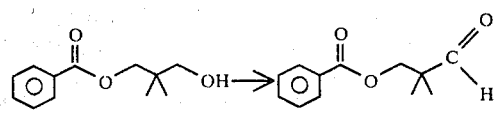

Using the apparatus of FIG. 10, a catalytic oxidation of alcohol (bulked fractions 2-11) prepared according to Example II is carried out. Maintaining the silver catalyst and reaction tube at a temperature of 450° C. (using furnace 16 and silver catalyst 18 on shaft 19 in reactor 17), oxygen held in vessel 120 is permitted to flow at a flow rate of 250 ml per minute through regulator 119, filter 118 and mass flow controller 117 through heater 112 while at the same time nitrogen at a flow rate of 100 ml per minute is permitted to flow through regulator 122, filter 123 and mass flow controller 116 whereupon the nitrogen flow joins the oxygen flow and the combined gasses (the nitrogen, oxygen and alcohol) are fed through heater 112 into reactor 17. Simultaneously, the bulked fractions 2-11 of the distillation product of Example II consisting of the compound having the structure:

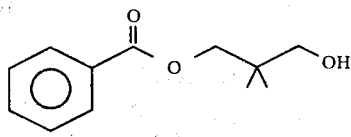

held in holding tank 101 is pumped through pump 104 into vaporizer 110 through heating tube 112 along with the oxygen and nitrogen. Simultaneously, water 103 held in holding tank 102 is pumped through pump 105 through tube 108 into vaporizer 111 and finally through heated tube 112 along with the oxygen, nitrogen and alcohol reactant (bulked fractions 2-11 of the distillation product of the reaction product of Example II consisting of the compound having the structure:

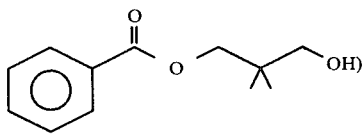

and finally into the reactor 17 and the silver catalyst 18 at 450° C. The flow rate of the bulked fractions 2–11 of the distillation product of the reaction product of Example II containing the compound having the structure:

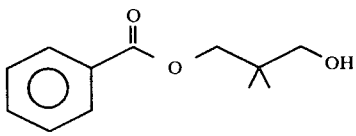

is 2 ml per minute (liquid). The liquid flow rate of the water is also 2 ml per minute.

The reaction product is condensed in heat exchanger 5 at 6 and is collected at location 1 in flask 2 which is cooled by ice bath 3. The volatiles are collected in flask 12 and cooled by dry ice bath 13. A vacuum 14 is supplied wherein the final volatiles are not permitted to escape but are collected at 15.

The detailed description of FIG. 10 is set forth in the section entitled "Detailed Description of the Drawings", supra.

The resulting product is trapped from a 10'×¼" Carbowax column programmed at 130° C., isothermal.

FIG. 8 is the NMR spectrum for the trap from this GLC, containing the compound having the structure:

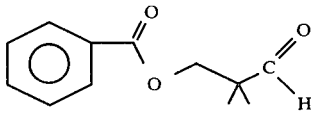

FIG. 9 is the infra-red spectrum for the product trapped from the GLC operated at the following conditions: 10'×¼" Carbowax column operated at 130° C. isothermal, having the structure:

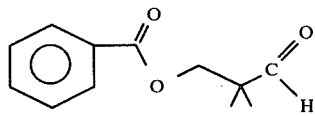

EXAMPLE IV

Preparation of 3-Hydroxy-2,2-Dimethylpropyl Ester of 2-Ethyl Hexanoic Acid

Reaction:

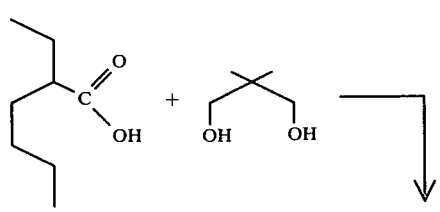

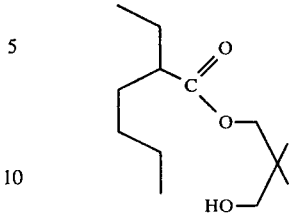

Into a 5 liter reaction flask equipped with heating mantle, stirrer, reflux condenser, thermometer and Bidwell trap, is placed 1,456 grams of 2,2-dimethyl-1,3-propanediol (14.0 moles); 1,100 ml of 2-ethyl hexanoic acid (7.0 moles), 700 ml toluene and 15 ml 93% concentrated sulfuric acid.

The reaction mass, with stirring, is heated to reflux and maintained at reflux at 126° C. while removing water of reaction. The refluxing is continued for a period of 9 hours at which point 300 ml of water has been removed from the reaction mass. When GLC analysis shows that the reaction is complete, the reaction mass is transferred to a 5 liter separatory flask and washed as follows:

(a) three 500 ml volumes of 15% aqueous sodium hydroxide;
(b) two 500 ml volumes of water;
(c) two 500 ml volumes of saturated sodium chloride solution.

The reaction mass is then distilled on a 1" Goodloe column yielding the following fractions:

| Fraction Number | Vapor Temp. (°C.) | Liquid Temp. (°C.) | Pressure mm/Hg. | Weight of Fraction (grams) |
| --- | --- | --- | --- | --- |
| 1 | 28/40 | 40/95 | 55/3 | |
| 2 | 107 | 128 | 3 | |
| 3 | 109 | 125 | 3 | 98 |
| 4 | 110 | 127 | 3 | 112 |
| 5 | 121 | 135 | 5 | 89 |
| 6 | 124 | 140 | 5 | 97 |
| 7 | 126 | 144 | 5 | 204 |
| 8 | 128 | 145 | 5 | 206 |
| 9 | 134 | 153 | 5 | 198 |
| 10 | 145 | 175 | 5 | 130 |
| 11 | 155 | 185 | 5 | |
| 12 | 165 | 190 | 5 | |
| 13 | 155 | 220 | 5 | |

Fractions 2–9 are bulked for subsequent oxidation.

FIG. 11 is the GLC profile (conditions: SE-30 column programmed at 100°–220° C.) for the reaction product prior to distillation.

FIG. 12 is the GLC profile for fraction 3 of the foregoing distillation product containing the compound having the structure:

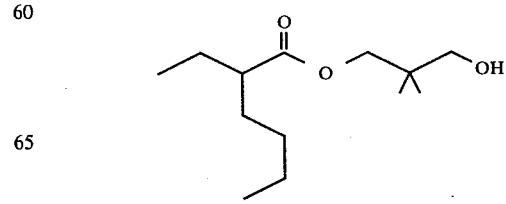

FIG. 13 is the NMR spectrum for bulked fractions 2-9 of the foregoing distillation containing the compound having the structure:

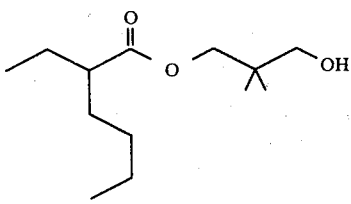

FIG. 14 is the infra-red spectrum for bulked fractions 2-9 of the foregoing distillation containing the compound having the structure:

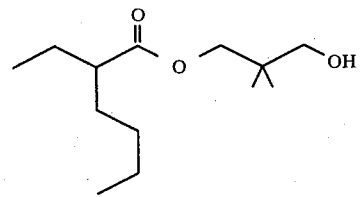

EXAMPLE V

Preparation of 2-Formyl-2-Methyl Propyl Ester of 2-Ethyl Hexanoic Acid

Reaction:

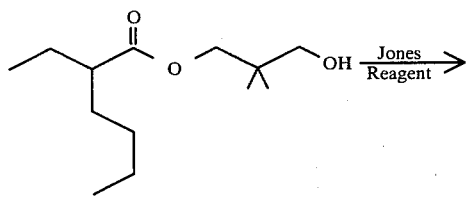

Into a 1 liter reaction flask equipped with cooling bath, stirrer, reflux condenser, thermometer, addition funnel and nitrogen blanket apparatus is placed 200 ml of acetone and 230 grams (1.0 moles) of the bulked fractions 2-9 of the distillation product of the reaction product of Example IV containing the compound having the structure:

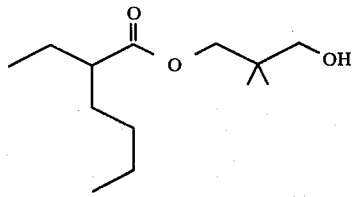

Jones reagent (sodium dichromate and sulfuric acid mixture) is added to the reaction mass slowly over a period of 0.5 hours while maintaining the mixture at a temperature in the range of 25°-30° C. At the end of the addition of the Jones reagent, the reaction mass is stirred at 25°-30° C. for a 7 hour period. At the end of the 7 hour period, GLC analysis indicates 60% conversion.

An additional 100 ml Jones reagent is then added and the reaction mass is permitted to exotherm to 51° C. GLC analysis indicates that reaction is complete.

The reaction product is added to 150 ml water and the resulting mixture is transferred to a separatory funnel. The aqueous phase is extracted with three 200 ml volumes of diethyl ether and the ether extracts are washed with three 500 ml portions of water followed by one 500 ml portion of a salt solution. The ether extracts and the organic phase are combined and the resulting product is stripped of solvent. The resulting product is then distilled on a 6" stone mirror column yielding the following fractions:

| Fraction Number | Vapor Temp. (°C.) | Liquid Temp. (°C.) | Pressure mm/Hg. | Reflux Ratio | Weight of Fraction (grams) |
|---|---|---|---|---|---|
| 1 | 66/95 | 125/142 | 1.5/2.0 | 2:1 | 20 |
| 2 | 93 | 147 | 2.0 | 2:1 | 21 |
| 3 | 104 | 164 | 2.0 | 2:1 | — |
| 4 | 140 | 200 | 2.0 | 2:1 | — |

Fraction 2 having a vapor temperature of 93° C. at 2.0 mm/Hg pressure is analyzed by means of GLC, NMR and IR analyses which analyses indicate that the structure of the compound contained therein is:

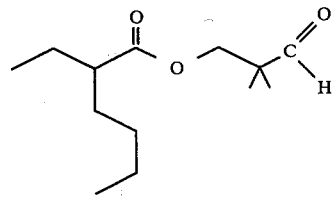

FIG. 5 is the GLC profile for the reaction product prior to distillation (conditions: SE-30 column programmed at 100°-220° C.). Peak 201 of FIG. 15 is the compound having the structure:

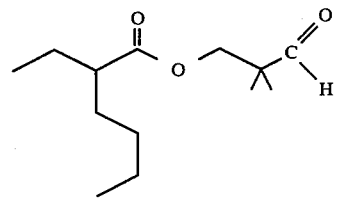

FIG. 16 is the GLC profile for fraction 1 of the foregoing distillation (conditions: SE-30 column programmed at 100°-220° C. at 8° C. per minute).

FIG. 17 is the NMR spectrum for the trap of Peak 201 of FIG. 15, the GLC profile, which is the compound having the structure:

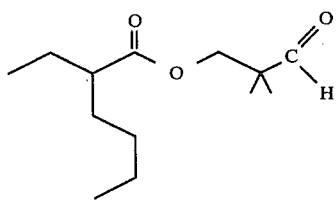

The foregoing reaction can also be carried out using, instead of the Jones reagent, oxygen or air as the oxidizing agent and using the apparatus of FIG. 10 as set forth in detail in Example III.

EXAMPLE VI

The following mixture is prepared:

| Ingredients | Example VI(A) | Example VI(B) |
|---|---|---|
| Phenylacetic acid | 70.0 | 70.0 |
| Coumarin | 20.0 | 0 |
| Phenylethylphenyl acetate | 100.0 | 100.0 |
| Phenyl ethyl alcohol | 5.0 | 5.0 |
| Benzyl benzoate | 100.0 | 100.0 |
| Dimethylphenylethyl carbinol | 10.0 | 10.0 |
| Methyl anthranilate | 5.0 | 5.0 |
| Beta ionone | 10.0 | 10.0 |
| Compound having the structure: prepared according to Example V | 0 | 12.0 |
| Compound having the structure: prepared according to Example III | 12.0 | 0 |

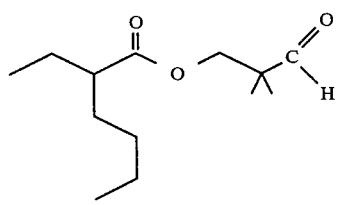

In Example VI(B), the compound having the structure:

prepared according to Example V imparts the ozoney, aldehydic, floral, green, spicy (coriander-like, cardamon-like and ginger-like) aroma to this honey formulation.

In Example VI(B), the compound having the structure:

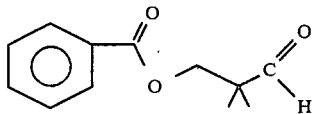

imparts the intense honey, tobacco aroma with coumarin-like and cumene-like notes and acts as a total replacer for coumarin in this formulation.

The compound having the structure:

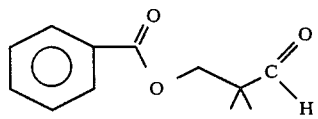

also acts as a replacer for cumene in those fragrance formulations where cumene has been previously used.

EXAMPLE VII

Preparation of Cosmetic Powder Compositions

Cosmetic powder compositions are prepared by mixing in a ball mill 100 grams of talcum powder with 0.25 grams of each of the substances set forth in Table II below. Each of the cosmetic powder compositions has an excellent aroma as described in Table II below.

TABLE II

| Substance | Aroma Description |
|---|---|
| Compound having the structure: prepared according to Example V | An ozoney, aldehydic, floral, green, spicy (coriander-like, cardamom-like and ginger-like) aroma. |
| Compound having the structure: | A fruity aroma. |
| Compound having the Sructure | A honey, tobacco aroma with coumarin-like and cumene-like nuances. |
| Compound having the Structure: | A fruity, woody aroma. |
| Perfume composition prepared according to Example VI(A). | A spicy, honey formulation with intense coriander-like, cardamom-like and ginger-like nuances and floral topnotes with herbaceous undertones. |
| Fragrance formulation prepared according to Example VI(B). | A honey, tobacco-like aroma with coumarin-like and cumene-like topnotes. |

EXAMPLE VIII

Perfumed Liquid Detergents

Concentrated liquid detergents (lysine salt of n-dodecylbenzene sulfonic acid as more specifically described in U.S. Pat. No. 3,948,818, issued on Apr. 6, 1976 incorporated by reference herein) with aroma nuances as set forth in Table II of Example VII, are prepared containing 0.10%, 0.15%, 0.20%, 0.25%, 0.30% and 0.35% of the substance set forth in Table II of Example VII. They are prepared by adding and homogeneously mixing the appropriate quantity of substance set forth in Table II of Example VII in the liquid detergent. The detergents all possess excellent aromas as set forth in Table II of Example VII, the intensity increasing with greater concentrations of substance as set forth in Table II of Example VII.

EXAMPLE IX

Preparation of Colognes and Handkerchief Perfumes

Compositions as set forth in Table II of Example VII are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25%, and 30% (in 80%, 85%, 90% and 95% aqueous food grade ethanol solutions). Distinctive and definitive fragrances are set forth in Table II of Example VII are imparted to the colognes and to the handkerchief perfumes at all levels indicated.

EXAMPLE X

Preparation of Soap Compositions

One hundred grams of soap chips (per sample) (IVORY ®, produced by the Proctor & Gamble Company of Cincinnati, Ohio), are each mixed with one gram samples of substances as set forth in Table II of Example VII until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table II of Example VII.

EXAMPLE XI

Preparation of Solid Detergent Compositions

Detergents are prepared using the following ingredients according to Example I of Canadian Pat. No. 1,007,948 (incorporated by reference herein):

| Ingredient | Percent by Weight |
|---|---|
| Neodol ® 45-11 (a $C_{15}$—$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table II of Example VII. Each of the detergent samples has an excellent aroma as indicated in Table II of Example VII.

EXAMPLE XII

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and the perfuming material are as follows:

1. A water "dissolvable" paper ("Dissolvo Paper");
2. Adogen 448 (m.p. about 140° F.) as the substrate coating; and
3. An outer coating having the following formulation (m.p. about 150° F.):
   57% $C_{20-22}$ HAPS
   22% isopropyl alcohol
   20% antistatic agent
   1% of one of the substances as set forth in Table II of Example VII.

Fabric softening compositions prepared according to Example I at column 15 of U.S. Pat. No. 3,632,396 having aroma characteristics as set forth in Table II of Example VII, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table II of Example VII is admixed in each case with the outer coating mixture, thereby providing a total aromatized outer coating weight ratio to substrate of about 0.5:1 by weight of the substrate. The aroma characteristics are imparted in a pleasant manner to the head space in a drier on operation thereof in each case using said dried-added fabric softener non-woven fabrics and these aroma characteristics are described in Table II of Example VII, supra.

EXAMPLE XIII

Hair Spray Formulations

The following hair spray formulation is prepared by first dissolving PVP/VA E-735 copolymer manufactured by the GAF Corporation of 140 West 51st St., New York, N.Y. in 91.62 grams of 95% food grade ethanol. 8.0 grams of the polymer is dissolved in the alcohol. The following ingredients are added to the PVP/VA alcoholic solution:

| | |
|---|---|
| Dioctyl sebacate | 0.05 weight percent |
| Benzyl alcohol | 0.10 weight percent |
| Dow Corning 473 fluid (prepared by the Dow Corning Corporation) | 0.10 weight percent |
| Tween 20 surfactant (prepared by ICI America Corporation) | 0.03 weight percent |
| One of the perfumery substances as set forth in Table II of Example VII, supra | 0.10 weight percent |

The perfuming substances as set forth in Table II of Example VII add aroma characteristics as set forth in Table II of Example VII which are rather intense and aesthetically pleasing to the users of the soft-feel, good-hold pump hair sprays.

EXAMPLE XIV

Conditioning Shampoos

Monamid CMA (prepared by the Mona Industries Company) (3.0 weight percent) is melted with 2.0 weight percent coconut fatty acid (prepared by Proctor & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "Composition A".

Gafquat® 755 N polymer (manufactured by GAF Corporation of 140 West 51st St., New York, N.Y.) (5.0 weight percent) is admixed with 0.1 weight percent sodium sulfite and 1.4 weight percent polyethylene glycol 6000 distearate produced by Armak Corporation. This material is "Composition B".

The resulting Composition A and Composition B are then mixed in a 50:50 weight ratio of A:B and cooled to 45° C. and 0.3 weight percent of perfuming substance as set forth in Table II of Example VII is added to the mixture. The resulting mixture is cooled to 40° C. and blending is carried out for an additional one hour in each case. At the end of this blending period, the resulting material has a pleasant fragrance as indicated in Table II of Example VII.

EXAMPLE XV

Perfumed Polymer

Scented polyethylene pellets having a pronounced honey aroma were prepared as follows:

75 pounds of polyethylene of a melting point of about 220° F. were heated to about 230° F. in a container of the kind illustrated in FIGS. 1 and 2 of U.S. Pat. No. 3,505,432, the disclosure of which is incorporated by reference herein. 25 pounds of the honey formulation of Example VI(A) were then quickly added to the liquified polyethylene, the lid was put in place and the agitating means were actuated. The temperature was maintained at about 225° F. and the mixing was continued for about 5-15 minutes. The valve was then opened to allow flow of the molten polyethylene enriched with the honey-containing material to exit through the orifices. The liquid falling through the orifices solidified almost instantaneously upon impact with the moving cooled conveyor. Solid polyethylene beads or pellets having a pronounced honey scent were thus formed. Analysis demonstrated that the pellets contained about 25% of the honey formulation of Example VI(A) so that almost no losses of the scenting substance did occur. These pellets may be called master pellets.

50 pounds of the honey-containing master pellets were then added to 1000 pounds of unscented polyethylene powder and the mass was heated to liquid state. The liquid was molded into thin sheets or films. The sheets or films had a pronounced honey aroma.

Patents Incorporated Herein By Reference

The following patents referred to supra are hereby incorporated herein by reference:
U.S. Pat. No. 3,632,396
U.S. Pat. No. 3,948,818
U.S. Pat. No. 3,505,432
Canadian Pat. No. 1,007,948

What is claimed is:

1. A process for augmenting or enhancing the aroma of a thermoplastic polymer comprising the step of intimately admixing with a polymer melt and aroma augmenting or enhancing quantity of at least one oxoalkyl ester defined according to the structure:

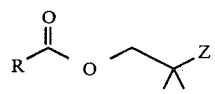

wherein Z is a moiety selected from the group consisting of carbinol having the structure:

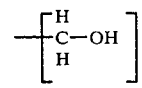

and carboxyaldehyde having the structure:

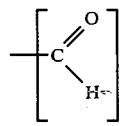

and R is selected from the group consisting of 3-heptanyl and phenyl whereby a heterogeneous mixture is produced wherein the perfume base is in the form of microdroplets intimately dispersed throughout the polymer melt phase and then chilling the polymer at such a rate as to cause the microdroplets of perfume oil to be retained as microdroplets which are interconnected with micropores among the microdroplets and to the surface of the resulting polymer.

2. The process of claim 1 wherein the oxoalkyl ester has the structure:

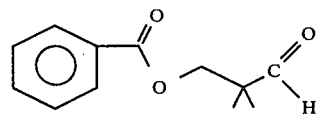

3. The process of claim 1 wherein the oxoalkyl ester has the structure:

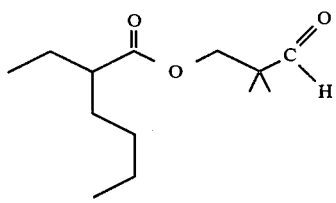

4. The process of claim 1 wherein the oxoalkyl ester has the structure:

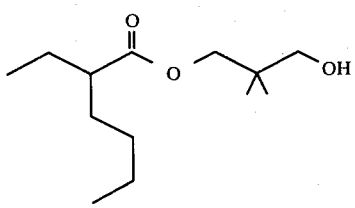

5. The process of claim 1 wherein the oxoalkyl ester has the structure:

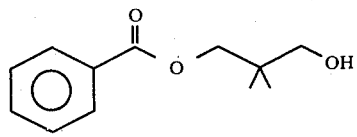

6. A method of scenting a polyolefin, which comprises:

(a) mixing a first amount of liquified polyolefin with a relatively large amount of scent-imparting material to form a flowable mass, said scent-imparting material being an oxoalkyl ester defined according to the structure:

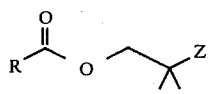

wherein Z is a moiety selected from the group consisting of carbinol having the structure:

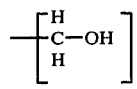

and carboxyaldehyde having the structure:

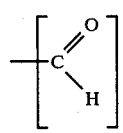

and R is selected from the group consisting of 3-heptanyl and phenyl;

(b) forming drops from said mass and causing substantially instantaneous solidification of said drops into polyolefin pellets having a relatively large amount of said scent-imparting material;

(c) melting said pellets with a second amount of said polyolefin, said second amount being larger than said first amount; and (d) solidifying the melt of (c).

7. The process of claim 6 wherein the oxoalkyl ester has the structure:

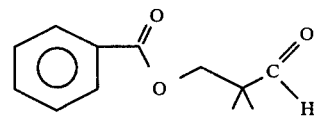

8. The process of claim 6 wherein the oxoalkyl ester has the structure:

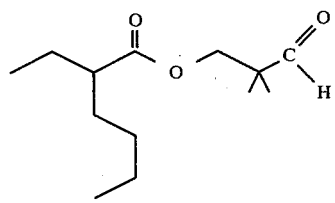

9. The process of claim 6 wherein the oxoalkyl ester has the structure:

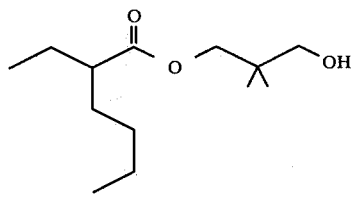

10. The process of claim 6 wherein the oxoalkyl ester has the structure:

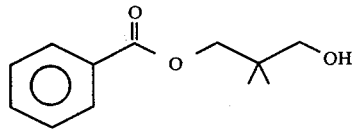

* * * * *